United States Patent [19]

Immer et al.

[11] 4,159,980

[45] Jul. 3, 1979

[54] PROCESS FOR PREPARING THE RELEASING HORMONE OF LUTEINIZING HORMONE (LH) AND OF FOLLICLE STIMULATING HORMONE (FSH), SALTS AND COMPOSITIONS THEREOF, AND INTERMEDIATES THEREFOR

[75] Inventors: Hans U. Immer; Verner R. Nelson, both of Montreal; Manfred K. Götz, Hudson, all of Canada

[73] Assignee: American Home Products Corporation, New York, N.Y.

[21] Appl. No.: 456,343

[22] Filed: Mar. 29, 1974

Related U.S. Application Data

[62] Division of Ser. No. 226,508, Feb. 15, 1972, Pat. No. 3,835,108.

[51] Int. Cl.$^2$ ............................................. C07C 103/52
[52] U.S. Cl. ........................ 260/112.5 LH; 260/112.5 R
[58] Field of Search ................ 260/112.5 LH, 112.5 R

[56] References Cited

U.S. PATENT DOCUMENTS 3,826,794  7/1974  Flouret ........................ 260/112.5 LH

*Primary Examiner*—Delbert R. Phillips
*Attorney, Agent, or Firm*—Arthur E. Wilfond

[57] ABSTRACT

A process for preparing the LH- and FSH-releasing hormone of the formula I

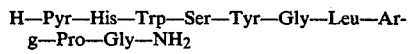

H—Pyr—His—Trp—Ser—Tyr—Gly—Leu—Arg—Pro—Gly—NH$_2$ which comprises the following steps: Condensing N-(5-oxo-L-prolyl)-L-histidine hydrazide by means of the azide method with L-tryptophan benzyl ester and treating the resulting compound with hydrazine hydrate to obtain N-[N-(5-oxo-L-prolyl)-L-histidyl]-L-tryptophan hydrazide (II); treating N-[O-benzyl-N-carboxy-L-tyrosyl]glycine N-benzyl ester with ethyl chloroformate to obtain the corresponding mixed anhydride which is reacted with t-butyl carbazate to obtain the corresponding 2-carboxyhydrazide t-butyl ester which is hydrogenolyzed to N-L-tyrosylglycine 2-carboxyhydrazide t-butyl ester; and condensing the latter with N-carboxy-L-seryl N-benzyl ester 2,4-dinitrophenyl ester followed by hydrogenolysis of the reaction product to obtain N-(N-L-seryl-L-tyrosyl)glycine 2-carboxyhydrazide t-butyl ester (III); condensing N-carboxy-L-proline N-benzyl ester with glycine ethyl ester in the presence of dicyclohexylcarbodiimide, treating the resulting product with ammonia and then hydrogenolyzing, to obtain 2-[(L-prolyl)amino]acetamide, which is condensed with N-carboxy-N$^G$-nitro-L-arginine N-t-butyl ester in the presence of dicyclohexylcarbodiimide and N-hydroxysuccinimide to obtain N-[N-(N-carboxy-N$^G$-nitro-L-arginyl)-L-prolyl)]glycinamide N-t-butyl ester (IV); or alternatively condensing L-proline methyl ester with N-carboxy-N$^G$-nitro-arginine N-t-butyl ester in the presence of dicyclohexylcarbodiimide, condensing the resulting product with glycine ethyl ester in the presence of dicyclohexylcarbodiimide, and treating the resulting product with ammonia to obtain the same compound IV as above; treating said compound IV with acid and then with N-carboxy-L-leucine N-benzyl ester 2,4,5-trichlorophenyl ester and hydrogenolyzing the resulting product in acetic acid, to obtain N-[N-[N-(N-L-leucyl)-L-arginyl]-L-prolyl]-glycinamide diacetate (V); condensing compound II with compound III by means of the azide method to obtain the hexapeptide N-[N-[N-[N-(5-oxo-L-prolyl)-L-histidyl]-L-tryptophyl]-L-seryl]-L-tyrosyl]glycine 2-carboxyhydrazide t-butyl ester, or condensing N-[N-(5-oxo-L-prolyl)-L-histidyl]-L-tryptophan with compound III in the presence of dicyclohexylcarbodiimide to obtain the same hexapeptide as above, and deprotecting and converting the latter to its trifluoroacetate salt (VI); and condensing compound V with compound VI by means of the azide method, to obtain the decapeptide of formula I which is isolated as the diacetate salt and optionally converted to other pharmaceutically acceptable salts.

1 Claim, No Drawings

PROCESS FOR PREPARING THE RELEASING HORMONE OF LUTEINIZING HORMONE (LH) AND OF FOLLICLE STIMULATING HORMONE (FSH), SALTS AND COMPOSITIONS THEREOF, AND INTERMEDIATES THEREFOR

This is a division of application Ser. No. 226,508, filed Feb. 15, 1972, now U.S. Pat. No. 3,835,108 granted Sept. 10, 1974.

BACKGROUND OF THE INVENTION

1. Field of Invention

This invention relates to a process for preparing the releasing hormone of luteinizing hormone (LH) and of follicle stimulating hormone (FSH) in the form of an acid addition salt, to salts thereof with pharamaceutically acceptable acids, to pharmaceutical compositions containing said LH and FSH-releasing hormone, and to intermediates obtained in said process.

LH and FSH are both gonadotrophic hormones elaborated by the pituitary gland of humans and of animals. LH together with FSH stimulates the release of estrogens from the maturing follicles in the ovary and induces the process of ovulation in the female. In the male, LH stimulates the interstitial cells and is for that reason also called interstitial cell stimulating hormone (ICSH). The follicle-stimulating hormone (FSH) induce maturation of the follicles in the ovary and together with LH, plays an important role in the cyclic phenomena in the female. FSH promotes the development of germinal cells in the testes of the male. Both LH and FHS are released from the pituitary gland by the action of LH- and FSH-releasing hormone, and there is good evidence that said releasing hormone is elaborated in the hypothalamus and reaches the pituitary gland by a neurohumoral pathway, see, e.g., Schally et al., Recent Progress in Hormone Research 24, 497 (1968).

The LH- and FSH--releasing hormone has been isolated from pig hypothalami and its constitution elucidated by Schally et al., Biochem. Biophys. Res. Commun. 43, 398 and 1334 (1971), who proposed the decapetide structure

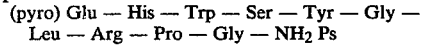

This constitution has been confirmed by syntheses (see below), and the LH- and FSH-releasing hormone may also be represented in a somewhat more modern terminology by the formula I

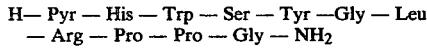

(I.)

2. Description of Prior Art

The LH- and FSH-releasing hormone has been synthesized by Sievertsson et al., Biochem. Biophys. Res. Commun. 44, 1566 (1971) by a combination of classical and solid-phase (Merrified) methods; the same hormone has also been synthesized by Geiger et al., ibid. 45 767 (1971) using a strictly classical method; by Matsuo et al., ibid. 45, 822 (1971) using a solid-phase method; and by Monahan et al., C. R. Acad. Sci., Ser. D, 273, No. 4,508 (1971) using a solid-phase method. In contradistinction to the processes of the references cited above the process of this invention is simpler and more efficient in giving considerably better over-all yields than any of the known procedures. It is a particular advantage of the process of this invention that it requires only a minimum of protective groups for the intermediates, especially where secondary functions are concerned. Thus, the hydroxyl group in serine does not have to be protected; the NH-groups in tryptophan and in histidine do not require protection; and no protection for the guanidino function in arginine and for the hydroxyl group of tyrosine is necessary in the later stages of the process. The process of this invention is thus also more convenient and less cumbersome than the processes of prior art. An added advantage of the process of this invention is the fact that the final step thereof consists in the condensation of two unprotected fragments, each of which is well defined, easy to purify, and each obtainable in a high state of purity. The final product thus obtained is the free, unprotected decapeptide which does not require any deprotective steps and is obtained in a high degree of purity and in good yields.

In the following text the term "lower alkyl" designates a straight or branched chain alkyl group containing from 1 — 6 carbon atoms and includes methyl, ethyl, propyl, isopropyl, n-butyl, sec-butyl, t-butyl and the like. The term "lower" indicates 1– 6 carbon atoms. The term "strong organic base" denotes aliphatic and heterocyclic tertiary nitrogen bases and includes triethylamine, dibutylmethylamine, N-methylpyrrolidine, N-methylpiperidine, N-methylpiperazine, N-methylmorpholine and the like; triethylamine is preferred. The term "halogenated hydrocarbon"denotes those having from 1–2 carbon atoms and includes methylene dichloride, ethylene dichloride, chloroform and the like; chloroform is preferred. The term "strong mineral acid "when used in conjunction with an anhydrous system, denotes hydrogen chloride, hydrogen bromide, and sulfuric acid; hydrogen chloride is preferred; when used in conjunction with an aqueous system the term includes any common mineral acid.

L-Pyroglutamic acid is the lactam of L-glutamic acid and has the structure of 5-oxo-L-proline.

Many of the methods used in the syntheses of peptide linkages are commonly designated by trivial names. Thus, the "azide method" comprises the reaction of an amino acid hydrazide having a suitably protected amino group with a nitrite, usually t-butyl or isoamyl nitrite, to obtain the corresponding azide which is then reacted with an amino acid having a free amino and a suitably protected carboxylic acid group, to obtain the desired peptide.

The condensation with dicyclohexylcarbodiimide comprises the reaction of an amino acid having a suitably protected amino and a free carboxylic acid group with another amino acid having a free amino and a suitably protected carboxylic acid group; the peptide linkage is formed with elimination of the elements of water and formatin of dicyclohexylurea which is easily removed from the reaction mixture. In the case where the free amino group of the second amino acid reacts only with difficulty, for example if the free amino group is secondary such as in proline, it is advantageous to add hydroxysuccinimide to the reaction to form the intermediate hydroxysuccinimide ester of the first amino acid which reacts readily with a secondary amino group to form the desired peptide linkage. In principle, this modification of the dicyclohexyl carbodiimide method involves an activation of the carboxylic acid group, and such activation is also obtained when the 4-nitrophenyl or 2,4-dinitrophenyl or 2,4,5-trichlorophenyl esters of the carboxylic acid are used instead of the free acid. Such esters are generally known as activated esters.

The protective groups in the process of this invention, and the conventional abbreviations by which they and the common amino acids are designated, are described in Schröder and Lübke, The Peptides, Academic Press, New York and London 1965.

SUMMARY OF THE INVENTION

The process of this invention is summarily described in the following steps:

N-(5-Oxo-L-prolyl)-L-histidine hydrazide, obtained as described by Gillessen et al., Helv. Chim. Acta 53, 63 (1970), is condensed by means of the azide method with a lower alkyl or aralkyl ester of L-tryptophan, preferably the benzyl ester obtained as described by Wilchek et al., J. Org. Chem. 28, 1874 (1963), to yield N-[N-(5-oxo-L-prolyl)-L-histidyl]-L-tryptophan benzyl ester. The latter is treated with hydrazine hydrate to yield N-[N-(5-oxo-L-prolyl)-L-histidyl]-L-tryptophan hydrazide (II).

A lower alkyl ester of N-[O-benzyl-N-carboxy-L-tyrosyl]glycine N-benzyl ester, preferably the methyl ester prepared as described by Morley, J. Chem Soc. (C), 2410,(1967) is hydrolyzed to the corresponding free acid which is converted to the corresponding mixed anhydride with ethyl chloroformate and treated with t-butyl carbazate to yield N-[O-benzyl-N-carboxy-L-tyrosyl]glycine N-benzyl ester 2-carboxyhydrazide t-butyl ester, and said last-named compound is hydrogenolyzed by means of hydrogen and a noble metal catalyst to yield N-L-tyrosylglycine 2-carboxyhydrazide t-butyl ester. Condensation of said last-named compound with an activated ester of N-carboxy-L-seryl N-benzyl ester, preferably the 2,4-dinitrophenyl ester prepared as described by Marchiori et al., Gazz. Chim. Ital., 93, 834 (1963) yields N-[N-(N-carboxy-L-seryl)-L-tyrosyl]glycine N-benzyl ester 2-carboxyhydrazide t-butyl ester which is hydrogenolyzed as above to yield N-(N-L-seryl-L-tyrosyl)glycine 2-carboxyhydrazide t-butyl ester (III).

N-carboxy-L-proline N-benzyl ester, prepared as described by Berger et al., J. Am. Chem. Soc., 76, 5552 (1954) is condensed with a glycine lower alkyl ester, preferably the ethyl ester, using dicyclohexylcarbodiimide as the condensing agent and the resulting product is treated with ammonia to obtain 2-[(N-carboxy-L-prolyl)amino]-acetamide N-benzyl ester. Said last-named compound is hydrogenolyzed and condensed with N-carboxy-N$^G$-nitro-L-arginine N-t-butyl ester, obtained as described by Hofmann et al., J. Am. Chem. Soc., 87, 620 (1965), using N-hydroxysuccinimide and dicyclohexylcarbodiimide as the condensing agents, to obtain N-[N-(N-carboxy-N$^G$-nitro-L-arginyl )-L-prolyl]glycinamide N-t-butyl ester (IV).

The same compound IV is also prepared by the following alternative route.

A lower alkyl ester of L-proline, preferably the methyl ester, and N-carboxy-N$^G$-nitro-arginine N-t-butyl ester, prepared respectively as described by Boissonas et al., Helv. Chim. Acta 44, 123 (1961) and by Hofmann et al. cited above, are condensed by means of dicyclohexylcarbodiimide to yield N-(N-carboxy-N$^G$-nitro-L-arginyl)-L-proline N-t-butyl ester. Said last-named compound is condensed with a glycine lower alkyl ester, preferably the ethyl ester, using dicyclohexylcarbodiimide as the condensing agent and the resulting product is treated with ammonia to obtain N-[N-(N-carboxy-N$^G$-nitro-L-arginyl)-L-prolyl]-glycinamide N-t-butyl ester (IV), identical with the product obtained as described above. The protective t-butoxycarbonyl group of said last-named compound is removed by treatment with acid and the resulting product is condensed with an activated ester of N-carboxy-L-leucine N-benzyl ester, preferably the 2,4,5-trichlorophenyl ester prepared as described by Kenner, et al., J. Chem. Soc., 761 (1968), to yield N-[N-[N-(N-carboxy-L-leucyl)-N$^G$-nitro-L-arginyl]-L-prolyl]glycinamide N-benzyl ester which is hydrogenolyzed in glacial acetic acid by means of hydrogen and a noble metal catalyst to remove the protective nitro and carbobenzoxy groups to yield the corresponding diacetate salt, N-[N-[N-(N-L-leucyl)-L-arginyl]-L-prolyl]-glycinamide diacetate (V).

N-[N-(5-Oxo-L-prolyl)-L-histidyl]-L-tryptophan hydrazide (II) and N-(N-L-seryl-L-tyrosyl)glycine 2-carboxyhydrazide t-butyl ester (III), both obtained as described above, are condensed by means of the azide method to yield the hexapeptide N-[N-[N-[N-(5-oxo-L-prolyl)-L-histidyl]-L-tryptophyl]-L-seryl]-L-tyrosyl]glycine 2-carboxyhydrazide t-butyl ester. The same compound is also obtained by condensation of N-[N-(5-oxo-L-prolyl)-L-histidyl]-L-tryptophan, obtained from the corresponding benzyl ester described above by hydrogenolysis, with N-(N-L-seryl-L-tyrosyl)glycine 2-carboxyhydrazide t-butyl ester (III), obtained as described above, using dicyclohexylcarbodiimide as the condensing agent. N-[N-[N-[N-(5-oxo-L-prolyl)-L-histidyl]-L-tryptophyl]-L-seryl]-L-tyrosyl]glycine 2-carboxyhydrazide t-butyl ester obtained by either of the above routes is treated with trifluoroacetic acid to yield the trifluoroacetic acid salt of the hexapeptide hydrazide, viz, N-[N-[N-[N-(5-oxo-L-prolyl)-L-histidyl]-L-tryptophyl]-L-seryl]-L-tyrosyl]glycine hydrazide trifluoroacetate (VI).

Said last-named compound (VI) is condensed by means of the azide method with N-[N-[N-(N-leucyl)-L-arginyl]-L-prolyl]-glycinamide diacetate (V) to yield the desired decapeptide 5-oxo-L-prolyl-L-histidyl-L-tryptophyl-L-seryl-L-tyrosylglycyl-L-leucyl-L-arginyl-L-prolylglycinamide (I) which is isolated in the form of its diacetate salt. The latter salt may be converted, if desired, into a different acid addition salt, e.g., a salt with a pharmaceutically acceptable acid, by treatment with the appropriate ion exchange resin in the manner described by Boissonas et al., Helv. Chim. Acta 43, 1349 (1960). Suitable ion exchange resins are strongly basic anion exchange resins, for example those listed in Greenstein and Winitz "Chemistry of the Amino Acids," John Wiley and Sons, Inc., New York and London 1961, Vol. 2, p. 1456. Basically substituted cross-linked polystyrene resins such as Amberlite IRA-400 or IRA-410 are preferred. The above diacetate may also be converted to a salt of low solubility in body fluids by treatment with a slightly water-soluble pharmaceutically acceptable acid. The acid addition salts of the LH- and FSH-releasing hormone produced by the process of this invention with pharmacalogically acceptable acids are biologically fully equivalent to the natural hormone.

The above sequence of reactions, omitting the successive introduction and removal of protective groups as well as the methods of condensation and the condensing agents used, is shown below in diagram 1.

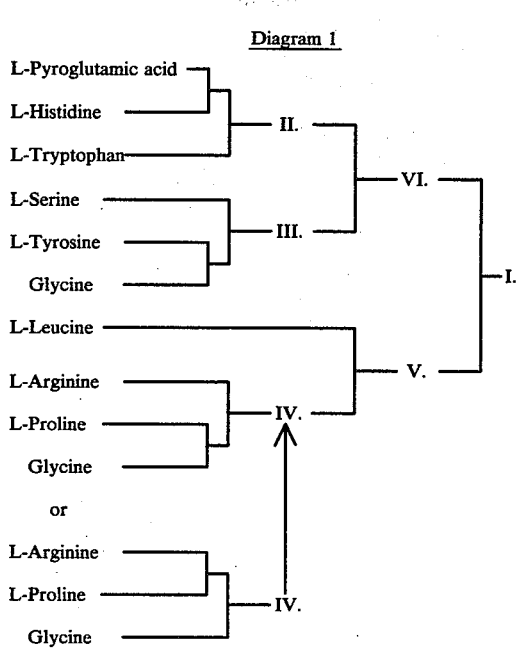

Diagram 1

DETAILED DESCRIPTION OF THE INVENTION

1. LH- and FSH-Releasing Activity

Figure 2:
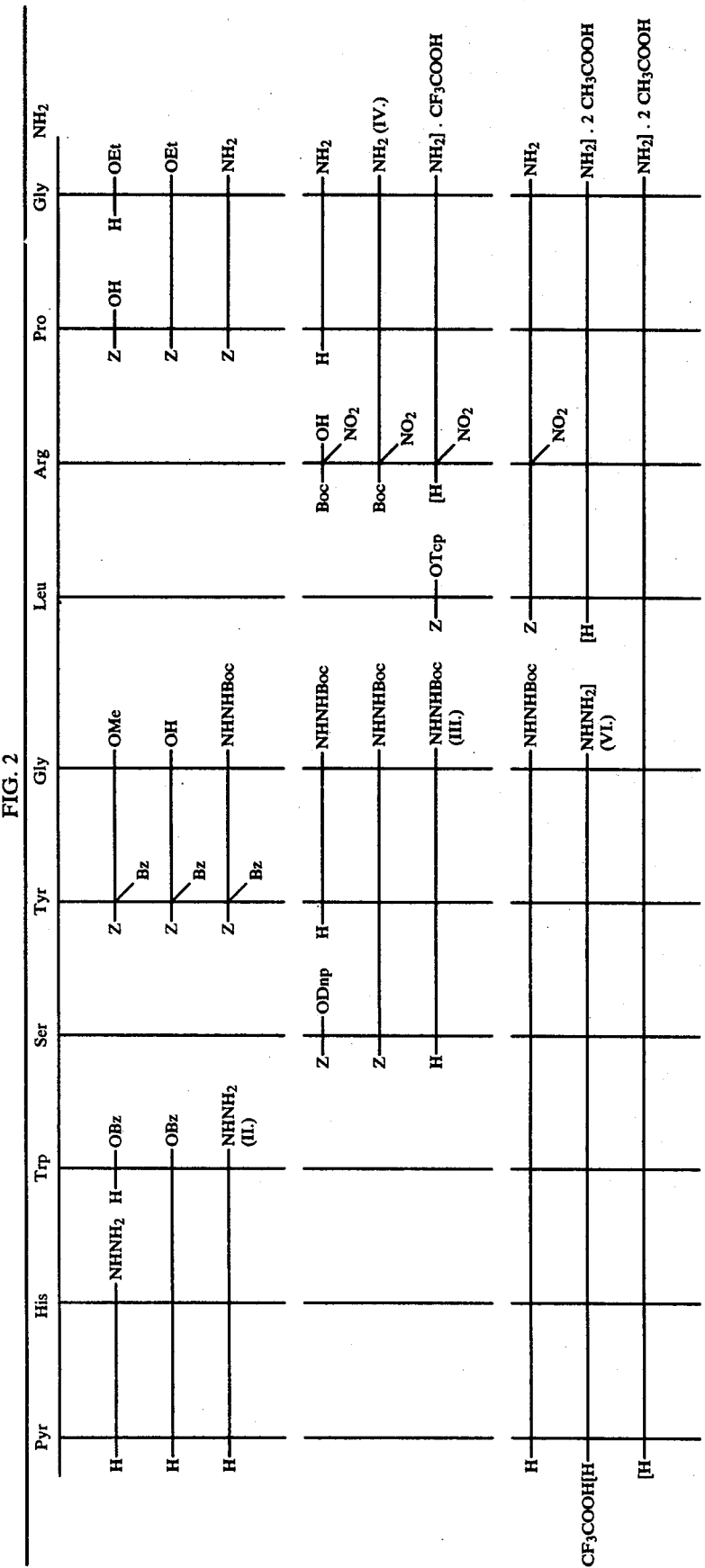

The synthetic product of formula I obtained by the process of this invention in the form of an acid addition salt possesses LH- and FSH-releasing properties and is as active as the natural hormone when tested in the radioimmunoassay described by Niswender et al. Proc. Soc. Exp. Biol. Med., 128, 807 (1968). It is equally active in the assay determining induction of ovulation in the hamster described by Arimura et al., Science 174, 511 (1971), and in a modification of the similar assay in the rat described by Arimura et al. in Endrocinology 80, 515 (1967).

The LH- and FSH-releasing properties of the hormone obtained by the process of this invention, which in turn induce ovulation in animals make the hormone useful in veterinary practice and in animal husbandry. It is often desirable to synchronize estrus in livestock, for example, cattle, sheep, or swine either in order to be able to mate all the females in a given group with a male of the desired genetic quality, or so as to be able to perform artificial insemination on a maximum number of females, both within a comparatively short period of time. In the past, this has been done by administering to the animals an ovulation-inhibiting agent, withdrawing administration of said agent shortly before the date chosen for mating or artificial insemination, and relying either upon the natural production of LH and FSH to induce ovulation and to produce estrus or by administering gonadotrophins. However, this procedure was not entirely satisfactory because ovulation at a predetermined time occured never in all the animals together but only in a certain proportion thereof when gonadotrophins were not used. On the other hand, the high cost of gonadotrophins and side effects encountered in their administration made this method impractical. It is now possible to obtain substantially complete synchronization of ovulation and of estrus, by treating the animals in a given group first with an ovulation inhibitor which is subsequently withdrawn, and then administering the LH- and FSH-releasing hormone produced by the process of this invention shortly before the predetermined period of time for mating or artificial insemination, so as to obtain ovulation and estrus within that time interval. The delay in the onset of ovulation and estrus following administration of the hormone produced by the process of this invention varies with the species of animal, and the optimal time interval has to be chosen for each species. For example, in rodents such as rats or hamsters ovulation takes place within 18 hours following administration of LH- and FSH-releasing hormone produced by the process of this invention.

The method described above for obtaining ovulation and estrus within a precisely predetermined time interval, so as to be certain of a successful mating is particularly important for breeders of race horses and of show animals, where the fees paid for the services of an exceptional male animal often amount to very considerable sums of money.

The LH- and FSH-releasing hormone produced by the process of this invention is also useful to increase the number of live births per pregnancy in livestock, for example, cattle, sheep or swine. For this purpose the LH- and FSH-releasing hormone is given in a series of parenteral doses, preferably by intravenous or subcutaneous injections, in the range of 1.0 mcg to 100 mcg per kilogram of body weight per day, 96 to 12 hours prior to expected estrus and subsequent mating. A priming injection of 1000 to 5000 IU of pregnant mares serum gonadotrophin may also be given one to four days prior to the above injection of LH- and FSH-releasing hormone. A similar treatment, with or without prior priming, is also useful for inducing puberty in farm animals.

When the hormone produced by the process of this invention is employed for the purpose of inducing ovulation and estrus or for inducing puberty in warm-blooded animals, especially in rodents such as rats or hamsters or in livestock, it is administered systemically, preferably parenterally, in combination with a pharmaceutically acceptable liquid or solid carrier. The proportion of the hormone is determined by its solubility in the given carrier, by the chosen route of administration, and by standard biological practice. For parenteral administration to animals the hormone may be used in a sterile aqueous solution which may also contain other solutes such as buffers or preservatives, as well as sufficient pharmaceutically acceptable salts or glucose to make the solution isotonic. The dosage will vary with the form of administration and with the particular species of animal to be treated and is preferably kept at a level of from 5 mcg to 100 mcg per kilogram body weight. However, a dosage level in the range of from about 10 mcg to about 50 mcg per kilogram body weight is most desirably employed in order to achieve effective results.

The hormone may also be administered in one of the long-acting, slow-release or depot dosage forms described below, preferably by intramuscular injection or by implantation. Such dosage forms are designed to release from about 0.5 mcg to about 50 mcg per kilogram body weight per day.

The LH- and FSH-releasing hormone produced by the process of this invention is also useful in human medicine. For exampale, human chorionic gonadotrophin (HCG) which contains mainly LH and some FSH has been used for over 30 years to treat certain endocrinological disorders such as disturbances of the cycle, amenorrhea, lack of development of secondary sex characteristics, and infertility in the female, or certain cases of hypogonadism, delayed puberty, cryptorchidism, and non-psychogenic impotence in the male. Lately, infertility in the human female has also been treated with human menopausal gondotrophin (HMG) which contains mainly FSH, followed by treatment with HCG. One of the disadvantages of the treatment of infertility in the human female with HCG or with HMG followed by HCG has become apparent in that such treatment often results in superovulation and unwanted multiple births, probably because of the impossibility of giving only the exact amounts of FSH and LH which are necessary for ovulation. The administration of the hormone produced by the process of this invention overcomes the above disadvantage, because the hormone causes release of LH and FSH by the pituitary only in the exact quantities which are required for normal ovulation. For that reason the hormone produced by the process of this invention is not only useful for the above purpose, but it is equally useful in the human female in the treatment of disturbances of the cycle, of amenorrhea, of hypogonadism, and of lack of development of secondary sex characteristics.

Furthermore, the LH- and FSH-releasing hormone produced by the process of this invention is also useful in contraception. For example, when the hormone is administered to a human female early in the menstrual cycle LH is released at that time and causes premature ovulation. The immature ovum is either not capable of being fertilized, or, if fertilization should nevertheless have taken place, it is highly unlikely that the fertilized ovum will become implanted because the estrogen-progestin balance required to prepare the endometrium is not present and the endometrium is not in the condition necessary for implantation. On the other hand, when the hormone is administered towards the end of the cycle the endometrium is disrupted and menstruation takes place.

In addition, the LH- and FSH-releasing hormone produced by the process of this invention is also useful in contraception by the "rhythm" method, which has always been relatively unreliable because of the impossibility of predetermining ovulation in the human female with the required degree of accuracy. Administration of the hormone at mid-cycle, i.e., at about the normally expected time for ovulation, induces ovulation shortly thereafter and makes the "rhythm" method both safe and effective.

The LH- and FSH-releasing hormone produced by the process of this invention is also useful as a diagnostic tool for distinguishing between hypothalamic and pituitary malfunctions or lesions in the human female. When administering the hormone to a patient suspected of such malfunctions or lesions and a rise in the level of LH is subsequently observed there is good indication to conclude that the hypothalamus is the cause of the malfunction and that the pituitary is intact. On the other hand, when no rise in circulating LH is seen following the administration of the hormone a diagnosis of pituitary malfunction or lesion can be made with a high degree of confidence.

In the human male, administration of the LH- and FSH-releasing hormone obtained by the process of this invention provides the amounts of LH (or ICSH) and of FSH necessary for normal sexual development in cases of hypogonadism or delayed puberty, and is also useful in the treatment of cryptorchidism. Furthermore, the FSH released by the administration of the hormone stimulates the development of germinal cells in the testes, and the hormone is useful in the treatment of non-psychogenic impotence.

When the LH- and FSH-releasing hormone obtained by the process of this invention in the form of an acid addition salt is employed in human medicine, it is administered systemically, either by intravenous, subcutaneous, or intramuscular injection, or by sublingual, nasal, or vaginal administration, in compositions in conjunction with a pharmaceutically acceptable vehicle or carrier.

For administration by injection or by the nasal route as drops or spray it is preferred to use the hormone in solution in a sterile aqueous vehicle which may also contain other solutes such as buffers or preservatives, as well as sufficient quantities of pharmaceutically acceptable salts or of glucose to make the solution isotonic.

The LH- and FSH-releasing hormone produced by the process of this invention may also be administered as nasal or vaginal powders or insufflations. For such purposes the hormone is administered in finely divided solid form together with a pharmaceutically acceptable solid carrier, for example a finely divided polyethylene glycol ("Carbowax 1540"), finely divided lactose, or, preferably only for vaginal administration, very finely divided silica ("Cab-O-Sil"). Such compositions may also contain other excipients in finely divided solid form such as preservatives, buffers, or surface active agents.

For sublingual or vaginal administration it is preferred to formulate the hormone in solid dosage forms such as sublingual tablets or vaginal inserts or suppositories with sufficient quantities of solid excipients such as starch, lactose, certain types of clay, buffers, and lubricating, disintegrating, or surface-active agents, or with semi-solid excipients commonly used in the formulation of suppositories. Examples of such excipients are found in standard pharmaceutical texts, e.g., in Remington's Pharmaceutical Sciences, Mack Publishing Company, Easton, Penna., 1970.

The dosage of the LH- and FSH-releasing hormone obtained by the process of this invention will vary with the form of administration and with the particular patient under treatment. Generally, treatment is initiated with small dosages substantially less than the optimum dose of the hormone. Thereafter, the dosage is increased by small increments until the optimum effect under the circumstances is reached. In general, the hormone obtained by the process of this invention is most desirably administered at a concentration level that will generally afford effective release of LH and of FSH without causing any harmful or deleterious side effects, and preferably at a level that is in a range of from about 1 mcg to about 100 mcg per kilogram body weight, although as aforementioned variations will occur. However, a dosage level that is in the range of from about 5 mcg to about 50 mcg per kilogram body weight is most desirably employed in order to achieve effective results.

It is often desirable to administer the hormone continuously over prolonged periods of time in long-acting, slow-release, or depot dosage forms. Such dosage forms may either contain a pharmaceutically acceptable salt of the hormone having a low degree of solubility in body fluids, for example one of those salts described below, or they may contain the hormone in the form of a water-soluble salt together with a protective carrier which prevents rapid release. In the latter case, for example, the hormone may be formulated with a non-antigenic partially hydrolyzed gelatin in the form of a viscous liquid; or the hormone may be adsorbed on a pharmaceutically acceptable solid carrier, for example zinc hydroxide, and may be administered in suspension in a pharmaceutically acceptable liquid vehicle; or the hormone may be formulated in gels or suspensions with a protective non-antigenic hydrocolloid, for example sodium carboxymethylcellulose, polyvinylpyrrolidone, sodium alginate, gelatine, polygalacturonic acids, for example, pectin, or certain mucopolysaccharides, together with aqueous or nonaqueous pharmaceutically acceptable liquid vehicles, preservatives, or surfactants. Examples of such formulations are found in standard pharmaceutical texts, e.g., in Remington's Pharmaceutical Sciences cited above. Long-acting, slow-release preparations of the hormone produced according to the process of this invention may also be obtained by microencapsulation in a pharmaceutically acceptable coating material, for example gelatine, polyvinyl alcohol or ethyl cellulose. Further examples of coating materials and of the processes used for microencapsulation are described by J. A. Herbig in Encyclopedia of Chemical Technology, Vol. 13, 2nd Ed., Wiley, New York 1967, pp. 436–456. Such formulations, as well as suspensions of salts of the hormone which are only sparingly soluble in body fluids, are designed to release from about 0.1 mcg to about 50 mcg of the hormone per kilogram body weight per day, and are preferably administered by intramuscular injection. Alternatively, some of the solid dosage forms listed above, for example certain sparingly water-soluble salts or dispersions in or adsorbates on solid carriers of salts of the hormones, for example dispersions in a neutral hydrogel of a polymer of ethylene glycol methacrylate or similar monomers cross-linked as described in U.S. Pat. No. 3,551,556 may also be formulated in the form of pellets releasing about the same amounts as shown above and may be implanted subcutaneously or intramuscularly.

Alternatively, slow-release effects over prolonged periods of time may also be obtained by administering the hormone obtained by the process of this invention as an acid addition salt in an intra-vaginal device or in a temporary implant, for example a container made of a non-irritating silicone polymer such as a polysiloxane, e.g., "Silastic," or of a neutral hydrogel of a polymer as described above, possessing the required degree of permeability to release from about 0.1 mcg to about 50 mcg per kilogram body weight per day. Such intra-vaginal or implant dosage forms for prolonged administration have the advantage that they may be removed when it is desired to interrupt or to terminate treatment.

2. Preparation of Compounds

The process of this invention is carried out in the following manner.

A solution of N-(5-oxo-L-prolyl)-L-histidine hydrazide (see Gillessen et al. cited above) in an inert anhydrous solvent, preferably a mixture of dimethylformamide and dimethylsulfoxide, is cooled to a temperature of from about −10° C. to about 5° C., mixed with a solution of a strong mineral acid, preferably hydrogen chloride, in an anhydrous ether or cyclic ether, preferably tetrahydrofuran, and the mixture is cooled to a temperature of from about −30° C. to about −20° C. An organic nitrite, preferably t-butyl nitrite or isoamyl nitrite, is added with stirring and the mixture is stirred for 20–60 minutes, preferably for about 30 minutes at a temperature of from about −30° C. to about −20° C. Sufficient quantities of a strong organic base, preferably triethylamine, are added with stirring to make the mixture alkaline, preferably pH 8–9. Keeping the temperature of the mixture within the range of about −30° C. to about −10° C., a solution in an inert solvent, preferably dimethylformamide, of a lower alkyl or aralkyl ester of L-tryptophan, preferably the benzyl ester (see Wilchek et al. cited above), is added in an amount of from 5–15 percent in excess over the molar equivalent. A molar excess of about 10 percent is preferred, and the mixture is stirred at about −30° C. to about −10° C. for 30–60 minutes and then in an ice bath for 16–24 hours, preferably for about 18 hours. Filtration of the precipitate, evaporation of the filtrate, and crystallization of the residue yields the corresponding N-[N-(5-oxo-L-prolyl)-L-histidyl]-L-tryptophan lower alkyl or aralkyl ester, the benzyl ester being preferred for purposes of isolation and purification. Said last-named compound, preferably in the form of benzyl ester, is dissolved in an anhydrous lower alkanol, preferably methanol, cooled to a temperature of from about −20° C. to about 0° C., preferably about −10° C., a molar excess of hydrazine hydrate is added with stirring and the mixture is stirred first at ice bath temperature, for 2–6 hours, preferably for about 3 hours, and then for 30–60 hours, preferably for about 40 hours, at room temperature (20°–25° C.). The precipitate is filtered and crystallized from a lower alkanol, preferably methanol, to yield N-[N-(5-oxo-L-proly)-L-histidyl]-L-tryptophan hydrazide (II.).

A lower alkyl ester of N-[O-benzyl-N-carboxy-L-tyrosyl]glycine N-benzyl ester, preferably the methyl ester (see Morley cited above) is dissolved in a lower alkanol or alkoxyalkanol, preferably methoxyethanol, a molar excess (5–20 percent excess, preferably about 15 percent excess) of an aqueous alkali metal hydroxide, preferably sodium hydroxide, is added and the mixture is stirred at room temperature for 0.5–2 hours, preferably for about one hour. The mixture is acidified with a strong mineral acid, preferably hydrochloric acid, the precipitate is filtered and crystallized from an aqueous lower alkanol, preferably methanol-water, to yield N-[O-benzyl-N-carboxy-L-tyrosyl]glycine N-benzyl ester. Said last-named compound is dissolved in an anhydrous ether or cyclic ether, preferably tetrahydrofuran, the solution is cooled to a temperature in the range of about −20° C., to about 0° C., preferably about −10° C., and substantially one molar equivalent of ethyl chloroformate is added. The mixture is stirred at about −10° C. for 5–30 minutes, preferably for about 10 minutes, and substantially one molar equivalent of t-butyl carbazate is added. The mixture is stirred first for 20–60 minutes, preferably for about 30 minutes, at about 0° C. and then for about 3–8 hours, preferably for about 5 hours, at room temperature (20° C.). The solvent is evaporated, the residue taken up in a substantially water-immiscible solvent, preferably a lower alkyl ester of a lower alkanoic acid, for example ethyl acetate, the solution washed, dried and evaporated, and the residue crystallized to yield N-[O-benzyl-N-carboxy-L-tyrosyl]glycine N-benzyl ester 2-carboxyhydrazide t-butyl ester. Said last-named compound is dissolved in an anhydrous lower alkanol, preferably methanol, a noble metal catalyst, e.g., palladium on charcoal, is added and the mixture is agitated in an atmosphere of hydrogen at room temperature until substantially 2 molar equivalents of hydrogen have been taken up. Filtration of the catalyst and evaporation of the filtrate yields a residue of N-L-tyrosylglycine 2-carboxyhydrazide t-butyl ester, used without purification in the subsequent step.

Said last-named compound is dissolved in an anhydrous halogenated hydrocarbon, e.g., chloroform, or preferably in dimethylformamide and the resulting solution is added, with exclusion of moisture, to a solution of an activated ester of N-carboxy-L-seryl N-benzyl ester, preferably the 2,4-dinitrophenyl ester (see Marchiori et al. cited above), previously cooled to about 0° C. The mixture is kept at about 0° C. for several days, preferably for about 3 days, the solvent is evaporated, the residue taken up in a mixture of a halogenated hydrocarbon, a lower alkanol, and a small amount of a weak organic base, preferably chloroform-methanol-pyridine, and the solution is subjected to chromatography, preferably on silica. Elution, evaporation of the eluates, and crystallization yields N-[N-(N-carboxy-L-seryl)-L-tyrosyl]glycine N-benzyl ester 2-carboxyhydrazide t-butyl ester. Said last-named compound is dissolved in a lower alkanol, preferably methanol, a noble metal catalyst, preferably palladium on charcoal, is added, and the mixture is agitated in an atmosphere of hydrogen at room temperature for 5–10 hours, preferably for about 7 hours until substantially one molar equivalent of hydrogen has been taken up. Filtration of the catalyst, evaporation of the filtrate, and crystallization of the residue yields N-(N-L-seryl-L-tyrosyl)-glycine 2-carboxyhydrazide t-butyl ester (III).

A solution of N-carboxy-L-proline N-benzyl ester (see Berger et al. cited above) and of an approximately equimolar amount of a glycine lower alkyl ester acid addition salt, preferably glycine ethyl ester hydrochloride, in a halogenated hydrocarbon solvent, preferably chloroform, is cooled to about 0° C. and a substantially equimolar amount of a strong organic base, preferably triethylamine, followed by a substantially equimolar amount of dicyclohexylcarbodiimide is added. The mixture is stirred at about 0° C. for 12–24 hours, preferably for about 16 hours, filtered, and the filtrate is washed, dried and evaporated. The residue is taken up in a lower alkanol saturated with ammonia at about 0° C., preferably methanol, and the solution is allowed to stand at about 0° C. for 48–72 hours. Evaporation of the solvent and crystallization yields 2-[(N-carboxy-L-prolyl-)amino]acetamide N-benzyl ester. Said last-named compound is dissolved in glacial acetic acid, a noble metal catalyst, preferably palladium on charcoal, is added and the mixture is agitated in an atmosphere of hydrogen until one molar equivalent of hydrogen has been taken up. Filtration and evaporation of the filtrate yields 2-[(L-prolyl)amino]acetamide which is dissolved in dimethylformamide containing a substantially equimolar amount of a strong organic base, preferably triethylamine, cooled and added at a temperature of from about −20° C. to about 0° C., preferably at about −10° C., to a solution of a N-carboxy-N$^G$-nitro-L-arginine N-lower alkyl ester, preferably the N-t-butyl ester (see Hofmann et al. cited above) in dimethylformamide containing about 2 molar equivalents of N-hydroxysuccinimide and about one molar equivalent of dicyclohexylcarbodiimide. The mixture is stirred at about −10° C. to about 5° C., preferably at about 0° C., first for 12–24 hours at about 0° C. and then for 24–48 hours at room temperature (20° C.–25° C.), evaporated, the residue is taken up in a mixture of a halogenated hydrocarbon and a lower alkanol, preferably chloroform and methanol, and is purified by chromatography on silica, to yield the corresponding N-lower alkyl ester of N-[N-(N-carboxy-N$^G$-nitro-L-arginyl)-L-prolyl]glycinamide, preferably the N-t-butyl ester (IV).

Alternatively, the same compound IV is also prepared as follows.

A lower alkyl ester acid addition salt of L-proline, preferably the methyl ester hydrochloride (see Boissonas et al. cited above), and an approximately equimolar amount of N-carboxy-N$^G$-nitro-L-arginine N-t-butyl ester (see Hofmann et al cited above) are dissolved in an anhydrous strongly polar solvent, for example dimethylsulfoxide, dimethylformamide, or acetonitrile, or mixtures thereof, preferably a mixture of acetonitrile and dimethylformamide, and a substantially equimolar amount of a strong organic base, preferably triethylamine, is added with stirring. The mixture is cooled to a temperature of from about −20° C. to about 0° C., preferably to about −10° C., a substantially equimolar amount of dicyclohexylcarbodiimide is added, the mixture is stirred at about 0° C. for 2–10 hours, preferably for 5 hours, and then for 8–24 hours, preferably for about 10 hours, at room temperature (20° C.–25° C.), filtered, and the filtrate evaporated. The residue is taken up in a halogenated hydrocarbon or in a substantially water-immiscible lower alkyl ester of a lower alkanoic acid, preferably chloroform or ethyl acetate, washed, evaporated, the residue taken up in a lower alkanol, preferably methanol, and stirred at room temperature for about 1–3 hours, with about 2 molar equivalents of an aqueous alkali metal hydroxide, preferably sodium hydroxide. The mixture is filtered, extracted with a halogenated hydrocarbon or a lower alkyl lower alkanoate, preferably chloroform or ethyl acetate, the aqueous phase is acidified, extracted as above, and the extracts are evaporated to yield N-(N-carboxy-N$^G$-nitro-L-arginyl)-L-proline N-t-butyl ester. Said last named compound is dissolved in dimethylformamide, an acid addition salt of a lower alkyl ester of glycine, preferably glycine ethyl ester hydrochloride, is added, the mixture is cooled to about 0° C., a substantially equimolar amount of a strong organic base, preferably triethylamine, and substantially one molar equivalent of dicyclohexylcarbodiimide, are added and the mixture is stirred, first at about 0° C. for 2–5 hours, preferably for about 3 hours, and then at room temperature for 12–24 hours, preferably for about 17 hours. Filtration, evaporation of the solvent, taking up the residue in a mixture of a halogenated hydrocarbon and a lower alkanol, preferably chloroform and methanol, followed by chromatography on silica, evaporation of the eluates, taking the residues into a lower alkanol saturated with ammonia at 0° C., preferably methanol, allowing the solution to stand at about 0° C. for several days, preferably for about 3 days, evaporating the solvent and crystallization yields N-[N-(N-caboxy-N$^G$-nitro-L-arginyl)-L-prolyl]glycinamide N-t-butyl ester (IV), identical with the product obtained by the different route described above.

Said last-named compound of formula IV, obtained by either of the routes described above, is dissolved in a strong acid commonly used for deprotection, preferably hydrogen chloride in a lower alkanol or in glacial acetic acid, or trifluoroacetic acid, the solution is kept at about 0° C. for 20–60 minutes, preferably for about 30 minutes, and is then added to about 5–15 parts by volume, preferably about 10 parts per volume, of an anhydrous inert water-immiscible ether-type solvent, such as a lower alkyl ether, preferably diethyl ether, to yield a precipitate of the corresponding salt of N-[N-(N$^G$-nitro-L-arginyl)-L-prolyl]glycinamide. The latter is filtered, dissolved in dimethylformamide containing a substantially equimolar amount of a strong organic base, preferably triethylamine, the solution stirred at about 0° C. for 15-30 minutes, and a substantially equimolar amount of an activated ester of N-carboxy-L-leucine N-benzyl ester preferably the 2,4,5-trichlorophenyl ester (see Kenner et al. cited above) is added. The mixture is allowed to stand first at about 0° C. for 24-48 hours and then at room temperature for 24-48 hours. Evaporation of the solvent, dissolving the residue in a mixture of a halogenated hydrocarbon and a lower alkanol, preferably chloroform-methanol, followed by chromatography on silica and evaporation of the eluate yields N-[N-[N-(N-carboxy-L-leucyl)-$N^G$-nitro-L-arginyl]-L-prolyl]glycinamide N-benzyl ester. Said last-named compound is dissolved in glacial acetic acid, a noble metal catalyst, preferably palladium on charcoal, is added and the mixture is agitated at room temperature in an atmosphere of hydrogen until substantially 4 molar equivalents of hydrogen have been taken up. Filtration and evaporation of the solvent yields N-[N-(N-L-leucyl)-L-arginyl]-L-prolyl]glycinamide diacetate (V) as an amorphous solid.

A solution of N-[N-(5-oxo-L-prolyl)-L-histidyl]-L-tryptophan hydrazide (II), obtained as described above, in an inert anhydrous solvent, preferably a mixture of dimethylformamide and dimethylsulfoxide, is cooled to a temperature of from about −10° C. to about 5° C., mixed with a solution of a strong mineral acid, preferably hydrogen chloride, in an anhydrous ether or cyclic ether, preferably tetrahydrofuran, and the mixture is cooled to a temperature of from about −30° C. to about −20° C. An organic nitrite, preferably t-butyl nitrite or isoamyl nitrite, is added with stirring in a substantially equimolar amount and the mixture is stirred for 20-60 minutes, preferably for about 30 minutes at a temperature of from about −30° C. to about −20° C. Sufficient quantities of a strong organic base, preferably triethylamine, are added with stirring to make the mixture alkaline, preferably pH 8-9. Keeping the mixture at a temperature of from about −30° C. to about −10° C., a solution of a substantially equimolar amount of N-(N-L-seryl-L-tyrosyl)glycine 2-carboxyhydrazide t-butyl ester (III), obtained as described above, in an inert anhydrous solvent, preferably dimethylformamide, is added with stirring, and agitation is continued for 30-60 minutes at about −30° C. to about −10° C., then at about 0° C. for another 30-60 minutes, and finally with cooling in an ice bath for 16-24 hours, preferably for about 18 hours, Filtration of the precipitate, evaporation of the filtrate, taking up the residue in a lower alkanol, preferably methanol, and precipitation by addition of an ether, preferably diethyl ether, followed by crystallization from a lower alkanol, preferably methanol, yields N-[N-[N-[N-[-(5-oxo-L-prolyl)-L-histidyl]-L-tryptophyl]-L-seryl]-L-tyrosyl]glycine-2-carboxyhydrazide t-butyl ester.

Alternatively, that same compound may also be prepared as follows:

A solution of N-[N-(5-oxo-L-prolyl)-L-histidyl]-L-tryptophan benzyl ester, obtained as described above is prepared in a lower alkanol, preferably methanol, or in glacial acetic acid, a noble metal catalyst, preferably palladium on charcoal, is added and the mixture is agitated in an atmosphere of hydrogen at room temperature for 10-30 hours, preferably for about 16 hours, until substantially one molar equivalent of hydrogen has been taken up. Filtration of the catalyst, evaporation of the filtrate, taking up the residue in a lower alkanol, preferably methanol, precipitation by addition of an ether, preferably diethyl ether, and filtration of the precipitate yields N-[N-(5-oxo-L-prolyl)-L-histidyl]-L-tryptophan, the same tripeptide as compound II described above except that the terminal carboxylic acid is unsubstituted. Said last-named compound is dissolved in an inert anhydrous solvent, preferably dimethylformamide, a substantially equimolar amount of N-(N-L-seryl-L-tyrosyl)glycine 2-carboxyhydrazide t-butyl ester (III, obtained as described above) is added, the mixture is cooled to about 0° C., a substantially one molar equivalent of dicyclohexylcarbodiimide is added and the mixture is stirred, first at about 0° C. for about 24 hours, and then at room temperature for 4-10 days, preferably for about 5 days. Filtration, evaporation of the solvent, taking up the residue in a mixture of a halogenated hydrocarbon and a lower alkanol, preferably chloroform and methanol, followed by chromatography on silica and evaporation of the eluate, taking up the residue in a lower alkanol, preferably methanol, and precipitation by addition of an ether, preferably diethyl ether, followed by filtration, yields N-[N-[N-[N-[N-(5-oxo-L-prolyl)-L-histidyl]-L-tryptophyl]-L-seryl]-L-tyrosyl]glycine 2-carboxyhydrazide t-butyl ester, identical with the same compound prepared as described above.

Said last-named compound, prepared by either of the routes described above, is dissolved in trifluoroacetic acid, preferably of about 90% strength, and the solution is stirred for 30-60 minutes first with cooling in an ice bath and then for another 30-60 minutes at room temperature. Precipitation with an ether, preferably diethyl ether, followed by crystallization from a lower alkanol, preferably methanol, yields the hexapeptide N-[N-[N-[N-[N-(5-oxo-L-propyl)-L-histidyl]-L-tryptophyl]-L-seryl]-L-tyrosyl]glycine hydrazide trifluoroacetate (VI).

Said last-named compound (VI) is dissolved in an inert anhydrous solvent, preferably a mixture of dimethylformamide and dimethylsulfoxide, and a solution of a strong mineral acid, preferably hydrogen chloride, in an anhydrous ether or cyclic ether, preferably tetrahydrofuran, is added with stirring at a temperature of from −10° C. to 5° C., preferably at about 0° C. The mixture is cooled to a temperature of from about −30° C. to about −10° C., preferably to about −20° C., a solution of a substantially equimolar amount of an organic nitrite, preferably t-butyl nitrite or isoamyl nitrite, in dimethylformamide is added and the mixture is stirred at about −30° C. to about −10° C. for 30-60 minutes. A sufficient amount of a strong organic base, preferably triethylamine, is added to make the mixture slightly alkaline, preferably pH 8-9, and a solution of a substantially equimolar amount of N-[N-[N-(N-L-leucyl)-L-arginyl]-L-prolyl]glycinamide diacetate (V, obtained as described above) in an anhydrous inert solvent, preferably dimethylformamide, is added together with a quantity of a strong organic base, preferably triethylamine, sufficient to neutralize the diacetate salt. The mixture is stirred at a temperature of from about −30° C. to about −10° C. for 30-60 minutes, then at about 0° C. for another 30-60 minutes, and finally with cooling in an ice bath for 16-24 hours. Filtration, evaporation of the filtrate, taking up the residue in a lower alkanol, preferably methanol, and precipitation by addition on an ether, preferably diethyl ether, yields the crude decapeptide which is purified by partition chromatography on a chemically modified cross-linked dextran ("Sephadex LH-20") using the lower phase of a n-butanolacetic acid-water mixture as solvent. Evaporation of the eluates, taking up the residue in a lower alkanol, preferably methanol, and precipitation by addition of an ether, preferably diethyl ether, yields the substantially pure decapeptide 5-oxo-L-prolyl-L-histidyl-L-tryptophyl-L-seryl-L-tyrosylglycyl-L-leucyl-L-arginyl-L-prolyl-glycinamide (I), isolated as the diacetate salt which shows the same amino acid analysis as the natural product and which is as potent as the latter in bioassays. If desired, the above diacetate salt may be converted into other acid addition salts, preferably those with pharmaceutically acceptable acids. For such purposes the above diacetate salt is treated with a strong basic anion exchange resin, for example one of those listed in Greenstein and Winitz "Chemistry of the Amino Acids," cited above, in the form of its salt with the acid of which it is desired to form the salt with the hormone. Elution yields the LH- and FSH-releasing hormone in the form of its salt with the corresponding desired acid. Preferred anion exchange resins are cross-linked polystyrene resins substituted with strongly basic groups such as Amberlite IRA-400 or IRA-410, and preferred acids are pharmaceutically acceptable acids, to obtain the corresponding pharmaceutically acceptable salts of the hormone.

If it is desired to obtain a salt of the decapeptide of formula I which is sparingly soluble in water or in body fluids, an acid addition salt thereof as obtained by the process of this invention is treated in aqueous solution with a pharmaceutically acceptable sparingly water-soluble acid, for example tannic, alginic, or pamoic acid, preferably in the form of one of their salts, for example the alkali metal salts. The hormone precipitates as the salt with the respective sparingly water-soluble acid and is isolated, for example by filtration or centrifugation.

The above sequence of reactions constituting the process of this invention and incorporating only the first alternative syntheses of the intermediates IV and VI described above is shown in FIG. 2, using the conventional abbreviations for the various amino acids and protective groups.

The following Examples will illustrate the invention. All compounds are identified by elementary analysis.

EXAMPLE 1

N-[N-(5-Oxo-L-Prolyl)-L-Histidyl]-L-Tryptophan Benzyl Ester

N-(5-Oxo-L-prolyl)-L-histidine hydrazide (0.840 g, 3 mmol) is dissolved in a solution at 0° C. of dry dimethylformamide (14 ml), dry dimethyl sulfoxide (10.5 ml) and 2.4 N anhydrous gaseous hydrogen chloride in dry tetrahydrofuran (7.5 ml). The solution is cooled to −20° C. and isoamyl nitrite (0.57 ml) is added with stirring. The solution is stirred for 30 minutes at −20° C. and is then cooled to −24° C. Triethylamine (3.2 ml) is slowly added until the solution is slightly alkaline pH 8–9. While stirring at −20° C., a solution of L-tryptophan benzyl ester (0.970 g, 3.3 mmol) in dry dimethylformamide (3.0 ml) is added. The solution is stirred at −20° C. for 30 minutes, at 0° C. for 30 minutes, and then at ice bath temperature for 18 hours. The solution is filtered and the precipitate is washed with dry dimethylformamide (2 × 2 ml). The combined filtrates are concentrated under reduced pressure at 40° C. The residue is dissolved in methanol (10 ml), diethyl ether (300 ml) is slowly added, and the precipitate is collected by filtration. The precipitate is once more dissolved in methanol (10 ml) and is precipitated by the addition of diethyl ether (300 ml). The precipitate is crystallized from methanol to give the title compound as a fine white powder, m.p. 250°–252° C., $[\alpha]_D^{25}$ + 1.6° (c=1.0, DMF).

In the same manner, when using t-butyl nitrite instead of isoamyl nitrite, or when using the methyl, ethyl, isopropyl or n-butyl ester of tryptophan, the corresponding methyl, ethyl, isopropyl or n-butyl ester of the title compound is also obtained.

EXAMPLE 2

N-[N-(5-Oxo-L-Prolyl)-L-Histidyl]-L-Tryptophan Hydrazide (II)

Hydrazine hydrate (99%, 1.5 ml) is slowly added to a stirred solution of N-[N-(5-oxo-L-prolyl)-L-histidyl]-L-tryptophan benzyl ester (Example 1, 0.868 g) in anhydrous methanol (150 ml) at −10° C. After stirring for 3 hours at ice bath temperature the solution is stirred for 40 hours at room temperature. The mixture is filtered and the cyrstalline precipitate is recrystallized from methanol to give the title compound as fine needles, m.p. 165°–169° C., $[\alpha]_D^{25}$ −24.6° (c=1.0, DMF).

In the same manner, when using the methyl, ethyl, isopropyl, or n-butyl ester of the starting material instead of the benzyl ester, the title compound is also obtained.

EXAMPLE 3

N-[N-(5-Oxo-L-Prolyl)-L-Histidyl]-L-Tryptophan

A mixture of N-[N-(5-oxo-L-prolyl)-L-histidyl]-L-tryptophan benzyle ester (Ex. 1, 0.300 g, 0.555 mmol) and 5 percent palladium on carbon (0.060 g) in galcial acetic acid (30 ml) is stirred rapidly under an atmosphere of hydrogen for 16 hours at room temperature. The mixture is filtered through diatomaceous earth ("Celite") and the filtrate is concentrated under reduced pressure. The residue is dissolved in methanol (10 ml) and diethyl ether (100 ml) is slowly added with vigorous stirring. The precipitate is collected, dissolved in methanol (10 ml) and diethyl ether (100 ml) is slowly added. The precipitate is collected, dissolved in methanol, treated with charcoal (0.20 g) and filtered through diatomaceous earth ("Celite"). The filtrate is evaporated to yield the title compound as a hard white glass which is used as such in a subsequent step.

EXAMPLE 4

N-[O-Benzyl-N-Carboxy-L-Tyrosyl]Glycine N-Benzyl Ester

To a solution of N-[O-benzyl-N-carboxy-L-tyrosyl]-glycine N-benzyl ester methyl ester (2 g, 0.0042 moles) in methoxyethanol (25 ml) aqueous sodium hydroxide (1N, 5 ml) is added with vigorous stirring. When complete solution of the precipitate is achieved (after about one hour), aqueous hydrochloric acid (1N, 5.25 ml) is added with cooling. The precipitate is washed with water and recrystallized from methanol-water to give the title compound with m.p. 166°–167° C., $[\alpha]_D^{25}$ −22.6° (c=1.0, DMF).

In the same manner, when using the ethyl, propyl, isopropyl or n-butyl ester of the starting material instead of the methyl ester, or when using methanol, ethanol, propanol, butanol, or 2-ethoxyethanol ("Cellosolve") as the solvent instead of methoxyethanol, the title compound is also obtained.

EXAMPLE 5

N[O- Benzyl-N-Carboxy-L-Tyrosyl]Glycine N-Benzyl Ester 2-Carboxyhydrazide t-Butyl Ester A solution of N-[O-benzyl-N-carboxy-L-tyrosyl]glycine N-benzyl ester (Example 4, 2.312 g, 0.005 moles) in dry tetrahydrofuran (12.5 ml) and triethylamine (0.7 ml, 0.005 moles) is cooled to −10° C. With stirring, ethyl chloroformate (0.48 ml, 0.005 moles) and after 10 minutes t-butyl carbazate (725 mg, 0.005 moles) are added and the mixture is kept for 30 minutes at 0° C. and for 5 hours at room temperature. After evaporation of the solvent the residue is taken up in ethyl acetate (100 ml), filtered and the filtrate washed successively with water (2 × 20 ml), aqueous ammonia (3 × 20 ml) and saturated sodium chloride solution (2 × 25 ml). The ethyl acetate layer is dried, evaporated under reduced pressure and the residue crystallized from benzene-hexane to give the title compound wth m.p. 88°–90° C.

EXAMPLE 6

N-L-Tyrosylglycine 2-Carboxyhydrazide t-Butyl Ester

To a solution of N-[O-benzyl-N-carboxy-L-tyrosyl]glycine N-benzyl ester 2-carboxyhydrazide t-butyl ester (Example 5, 2.88 g, 0.005 moles) in dry methanol (40 ml) palladium on charcoal (5%, 200 mg) is added. the hydrogenation is carried out with the hydrogenation vessel connected to a stirred solution of sodium hydroxide (4N, 40 ml) to absorb carbon dioxide. After 4 hours the theoretical amount of hydrogen is consumed. The catalyst is filtered off through diatomaceous earth ("Celite"), the filtrate evaporated under reduced pressure at 30° C. and the title compound obtained as an oily residue which is used without purification in the next step.

In the same manner, when using platinum instead of palladium as a catalyst, the title compound is also obtained.

EXAMPLE 7

N[N-(N-Carboxy-L-Seryl)-L-Tyrosyl]Glycine N-Benzyl Ester 2-Carboxyhydrazide t-Butyl Ester To a solution of N-carboxy-L-seryl N-benzyl ester 2,4-dinitrophenyl ester (1.6 g, 0.004 moles) in dry dimethylformamide (10 ml) cooled to 0° C. and protected from moisture a solution of N-L-tyrosylglycine 2-carboxyhydrazide t-butyl ester (Example 6, 1.689 g, 0.005 moles) in dry dimethylformamide is added. The solution is kept at 0° C. for three days. After evaporation of the solvent the residue is taken up in chloroform-methanol-pyridine (100:25:1) and chromatographed over a 100 fold amount of silica. The pure material is taken into a small amount of methanol and precipitated by addition of ether to give the pure title compound with m.p. 65°–95° C., $[\alpha]_D^{25}$ −13.1° (c=1.0, DMF).

EXAMPLE 8

N-(N-L-Seryl-L-Tyrosyl)glycine 2-Carboxyhydrazide t-Butyl Ester (III)

A mixture of N-carboxy-L-seryl-L-tyrosylglycine N-benzyl ester 2-carboxyhydrazide t-butyl ester (Example 7, 0.96 g) and 5% palladium on carbon (0.090 g) in methanol (35 ml) is rapidly stirred under an atmosphere of hydrogen for 7 hours at room temperature in the same manner as described in Example 6 (hydrogen absorbed 49 ml). The mixture is filtered through diatomaceous earth ("Celite") and the filtrate is concentrated under reduced pressure. The residue is crystallized from methanol-diethyl ether to give the title compound as fine white prisms with m.p. 132°–135° C., $[\alpha]_D^{25}$ −5.4° (c=1.0, DMF).

In the same manner, but using platinum instead of palladium as a catalyst, the title compound is also obtained.

EXAMPLE 9

2-[(N-Carboxy-L-Prolyl)Amino]Acetamide N-Benzyl Ester

To a stirred solution of N-carboxy-L-proline N-benzyl ester (12.5 g, 0.05 moles) and glycine ethyl ester hydrochloride (7.26 g, 0.052 moles) in chloroform (100 ml) at 0° C., triethylamine (7.28 ml, 0.052 moles) followed by dicyclohexylcarbodiimide (10.7 g, 0.052 moles) is added. After stirring for 16 hours at 0° C. the precipitate is filtered off and the filtrate washed successively with water (50 ml), hydrochloric acid (1N, 50 ml), water (50 ml), and saturated sodium chloride solution (50 ml), dried with magnesium sulfate and evaporated. The residue is taken up in methanol saturated with ammonia at 0° C. (150 ml) and left at this temperature for 48 hours. After evaporation of the solvent under reduced pressure the residue is recrystallized from methanol-ether to yield the title compound with m.p. 112°–115° C., further recrystallized from methanol-isopropyl ether to m.p. 116°–120° C., $[\alpha]_D^{25}$ −43.8° (c=1.0, MeOH)

In the same manner, but using the methyl, propyl, isopropyl, or n-butyl ester of glycine instead of the ethyl ester, the title compound is also obtained.

EXAMPLE 10

2-[(L-Prolyl)Amino]Acetamide Hydrochloride

A solution of 2-[(N-carboxy-L-prolyl)amino]acetamide N-benzyl ester (Ex. 9, 610 mg, 2 mmoles) in glacial acetic acid (8 ml) containing hydrogen chloride (2 mmoles) is agitated with palladium on charcoal (5%, 50 mg) in an atmosphere of hydrogen in the same manner as described in Example 6 until one molar equivalent of hydrogen has been consumed. Filtration, evaporation of the filtrate and drying of the residue under reduced pressure gives the title compound which is used as such in the subsequent step.

In the same manner, but using platinum instead of palladium as a catalyst, the title compound is also obtained.

Also in the same manner, but using hydrogen bromide or sulfuric acid instead of hydrogen chloride, the corresponding hydrobromide or sulfate salts of the title compound are obtained.

EXAMPLE 11

N-[N-(N-Carboxy-$N^G$-Nitro-L-Arginyl]-L-Prolyl]-Glycinamide N-t-Butyl Ester (IV)

To a solution of N-carboxy-$N^G$-nitro-arginine N-t-butyl ester (607 mg, 1.9 mmole) and N-hydroxysuccinimide (437 mg, 3.8 mmole) in dimethylformamide (5 ml) at −10° C. dicyclohexylcarbodiimide (388 mg., 1.9 mmoles) is added. The mixture is stirred 1 hour at −10° C., 2 hours at 0° C. and 2 hours at room temperature. 2-[(L-Prolyl)-amino]acetamide hydrochloride obtained as the residue in Example 10 is dissolved in dimethylformamide (4 ml) at 0° C., triethylamine (0.38 ml) is added and this solution is added to the solution of the active ester described above at about 0° C. The mixture is stirred for 14 hours at 0° C. and for 24 hours at room temperature, then evaporated under reduced pressure to dryness. The residue is taken up in chloroform-methanol (100:15) and chromatographed over 100 g of silica. The pure title compound separates from absolute ethanol as a gelatinous precipitate, sintering at about 165° C., $[\alpha]_D^{25}$ −25.80 (c = 1.0, DMF).

In the same manner, but using the hydrobromide or sulfate salts of 2-[(L-prolyl)amino]acetamide instead of the hydrochloride salt, the title compound is obtained.

EXAMPLE 12

N-(N-Carboxy-$N^G$-Nitro-L-Arginyl)-L-Proline N-t-Butyl Ester

To a solution of L-proline methyl ester hydrochloride (5.85 g, 35.4 mmoles) and N-carboxy-$N^G$-nitro-arginine N-t-butyl ester (9.4 g, 29.4 mmoles) in acetonitrile (10 ml) and dimethylformamide (25 ml) triethylamine (4.95 ml) is added. The mixture is cooled to −10° C. and dicyclohexylcarbodiimide (7.25 g, 35.2 mmoles) is added. After 5 hours at 0° C. and 10 hours at room temperature the mixture is filtered and the filtrate evaporated to dryness under reduced pressure. The resulting residue is taken in ethyl acetate (300 ml) and washed successively with citric acid solution (10%, 2×90 ml) ammonia solution (1N, 3×90 ml), and saturated sodium chloride solution (90 ml). The oily residue left after drying and evaporation of the organic layer is taken in methanol (88 ml). Aqueous sodium hydroxide solution (1N, 88 ml) is added and the mixture is stirred for one hour at room temperature. After filtration the filtrate is extracted with ethyl acetate (3×150 ml). The aqueous phase is acidified with hydrochloric acid (4N, 30 ml) and extracted with ethyl acetate (3×150 ml). The combined ethyl acetate extracts are washed with saturated sodium chloride solution, dried with magnesium sulfate and evaporated under reduced pressure. The title compound is obtained as an amorphous residue which shows one main spot in electrophoresis in an aqueous buffer at pH 5.3 containing pyridine (1%) and acetic acid (0.32%) at 4,000 volt. It is used without further purification in the next step.

In the same manner, when using the ethyl, isopropyl, or n-butyl ester of L-proline instead of the methyl ester, the title compound is also obtained.

EXAMPLE 13

N-[N-(N-Carboxy-N$^G$-Nitro-L-Arginyl)-L-Prolyl]-Glycinamide N-t-Butyl Ester (IV)

N-(N-Carboxy-N$^G$-nitro-L-arginyl)-L-proline N-t-butyl ester (Ex. 12, 7.11 g, 17.1 mmoles) and glycine ethyl ester hydrochloride (2.5 g, 17.1 mmoles) are dissolved in dimethylformamide (45 ml). With stirring at 0° C. triethylamine (2.4 ml) and after 10 minutes dicyclohexylcarbodiimide (3.52 g, 17.1 mmoles) are added. The mixture is stirred for 3 hours at 0° C. and for 17 hours at room temperature, then filtered and the filtrate evaporated to dryness under reduced pressure. After chromatography on silica (500 g) with chloroform-methanol (100:8) as solvent and evaporation an oily product is obtained. It is dissolved in methanol saturated with ammonia at 0° C. and left at this temperature for three days. The solvents are evaporated and the residue triturated with ethyl acetate. The resulting title compound precipitates from absolute ethanol as a gelatinous product with m.p. 153°–163° C., $[\alpha]_D^{25} -26°$ (c = 1.0, DMF), identical with the same compound obtained as described in Example 11.

In the same manner, when using the methyl, isopropyl, or n-butyl ester of glycine instead of the ethyl ester, the title compound is also obtained.

EXAMPLE 14

N-[N-[N-(N-Carboxy-L-Leucyl)-N$^G$-Nitro-L-Arginyl]-L-Prolyl]Glycinamide N-Benzyl Ester A solution of N-[N-(N-carboxy-N$^G$-nitro-L-arginyl)-L-prolyl]-glycinamide t-butyl ester (Exs. 11 or 13, 817 mg, 1.76 mmoles) in trifluoroacetic acid (5 ml) is kept for 30 minutes at 0° C. The solution is added dropwise to cold absolute ether (50 ml), the precipitate of N-[N-(N$^G$-nitro-L-arginyl)-L-prolyl]glycinamide trifluoroacetate is filtered off and washed well with dry ether. After drying under reduced pressure the solid is taken in dimethylformamide (6 ml) containing triethylamine (0.245 ml) and stirred for 15 minutes at 0° C. To this solution a solution of N-carboxy-L-leucine N-benzyl ester 2,4,5-trichlorophenyl ester (860 mg, 1.96 mmoles) and a drop of acetic acid are added and the mixture is left for 24 hours at 0° C. and for 24 hours at room temperature. After evaporation to dryness under reduced pressure the residue is taken up in chloroform-methanol (100:15) and chromatographed over 150 g of silica. The chromatographically pure title compound is obtained as an amorphous solid, dissolved in methanol (3 ml) and precipitated by adding this solution to cold isopropyl ether (50 ml), to give the title compound with $[\alpha]_D^{25} -38.4°$ (c = 1.0, DMF).

In the same manner as described above, but using instead of trifluoroacetic acid hydrogen chloride in a lower alkanol or in glacial acetic acid, the hydrochloride of N-[N-(N$^G$-nitro-L-arginyl)-L-prolyl]glycinamide is obtained and is converted to the title compound in the same manner as described above.

In the same manner the title compound is also obtained when the 4-nitrophenyl or 2,4-dinitrophenyl esters of N-carboxy-L-leucine N-butyl ester are used instead of the 2,4,5-trichlorophenyl ester.

EXAMPLE 15

N-[N-[N-(N-L-Leucyl)-L-Arginyl]-L-Prolyl]-Glycinamide Diacetate (V)

A solution of N-[N-[N-(N-carboxy-L-leucyl)-N$^G$-nitro-L-arginyl]-L-prolyl]glycinamide N-benzyl ester (Ex. 14, 805 mg, 1.3 mmoles) in glacial acetic acid (5 ml) containing palladium on charcoal catalyst (5%, 300 mg) is agitated under hydrogen in the same manner as described in Example 6. The reaction mixture is filtered through diatomaceous earth ("Celite"), the filtrate concentrated under reduced pressure and added dropwise with stirring to dry ether at 0° C. The amorphous precipitate is filtered, washed well with ether and dried under reduced pressure, to give the title compound which is homogeneous in thin layer chromatography on silica using ethyl acetate-acetic acid-n-butanol-water (1:1:1:1) as the solvent, and by electrophoresis at pH 1.6 in 8% aqueous formic acid at 4,000 volt or at pH 5.3 in an aqueous buffer containing 1% pyridine and 0.32% acetic acid at 4,000 volt.

In the same manner, when using platinum instead of palladium as a catalyst, the title compound is also obtained.

EXAMPLE 16

N-[N-[N-[N-[N-(5-Oxo-L-Prolyl)-L-Histidyl]-L-Tryptophyl]-L-Seryl]-L-Tyrosyl]glycine 2-Carboxyhydrazide t-Butyl Ester

Method A.

N-[N-(5-Oxo-L-prolyl)-L-histidyl]-L-tryptophan hydrazide (II., Ex. 2, 0.655 g, 1.40 mmole) is dissolved at 0° C. in a solution of dry dimethylformamide (7 ml), dry dimethyl sulfoxide (5.9 ml) and 2.4 N anhydrous gaseous hydrogen chloride in dry tetrahydrofuran (3.5 ml). The solution is cooled to −20° C. and isoamyl nitrite (0.206 ml, 1.53 mmol) is added with stirring. The solution is stirred for 30 minutes at −20° C. and is cooled to −25° C. Triethylamine (1.3 ml) is slowly added until the solution is slightly alkaline, pH 8–9. While stirring at −20° C., a solution of N-(N-L-seryl-L-tyrosyl)glycine 2-carboxyhydrazide t-butyl ester (III., Ex. 8, 0.617 g, 1.40 mmol) in dry dimethylformamide (6 ml) is added. The solution is stirrred at −20° C. for 30 minutes at 0° C. for 30 minutes, and at ice bath temperature for 18 hours. The solution is filtered and the precipitate is washed with dry dimethylformamide (2×2 ml). The combined filtrates are concentrated under reduced pressure at 40° C. The residue is dissolved in methanol (5 ml), diethyl ether (500 ml) is slowly added, and the precipitate is collected by filtration. The precipitate is dissolved in methanol (5 ml) and is precipitated by addition of diethyl ether (500 ml). The collected precipitate is crystallized from methanol to give the title compound as a fine white powder with m.p. 182° C. (dec).

In the same manner, when using t-butyl nitrite instead of isoamyl nitrite, the title compound is also obtained.

Method B.

N-[N-(5-oxo-L-prolyl)-L-histidyl]-L-trptophan (Ex. 3, 0.133 g, 0.294 mmol) and N-(N-L-seryl-L-tyrosyl)glycine 2-carboxyhydrazide t-butyl ester (III, Ex. 8, 0.129 g, 0.294 mmol) are dissolved in anhydrous dimethylformamide (5 ml). With stirring at 0° C., dicyclohexylcarbodiimide (0.061 g, 0.294 mmol) is added. The solution is stirred for 24 hours at 0° C. and for 5 days at room temperature, then filtered and the filtrate evaporated to dryness under reduced pressure. After chromatography on silica (20 g) with chloroform-methanol (2:1) as solvent the combined fractions are concentrated under reduced pressure. The residue is dissolved in methanol (2 ml), diethyl ether (100 ml) is slowly added, and the precipitate is collected by filtration. The resulting product is identical with the title compound obtained as described above.

EXAMPLE 17

N-[N-[N-[N-[N-(5-Oxo-L-Prolyl)-L-Histidyl]-L-Tryptophyl]-L-Seryl]-L-Tyrosyl]glycine Hydrazide Trifluoroacetate (VI)

A solution of N-[N-[N-[N-[N-(5-oxo-L-prolyl)-L-histidyl]-L-tryptophyl]-L-seryl]-L-tyrosyl]glycine 2-carboxyhydrazide t-butyl ester (Example 16, 0859 g, 0.982 mmol) in 90 percent trifluoroacetic acid (27 ml) is stirred at ice bath temperature for 30 minutes and then at room temperature for 30 minutes. The solution is slowly added to a stirred solution of diethyl ether (700 ml). The precipitate is collected and crystallized from methanol to yield the title compound as a fine white powder with mp 200° C. (dec.), $[\alpha]_D^{25}$ −21.2° (c = 1.0, water).

EXAMPLE 18

5-Oxo-L-Prolyl-L-Histidyl-L-Tryptophyl-L-Seryl-L-Tyrosylglycyl-L-Leucyl-L-Arginyl-L-Prolylglycinamide (I) Diacetate N-[N-[N-[N-[N-(5-Oxo-L-prolyl)-L-histidyl]-L-tryptophyl]-L-seryl]-L-tyrosyl]glycine hydrazide trifluoroacetate (VI, Ex. 17, 0.840 g, 0.762 mmol) is dissolved at 0° C. in a mixture of dry dimethylformamide (3.7 ml), dry dimethylsulfoxide (3.3 ml) and 1.65 N anhydrous gaseous hydrogen chloride in dry tetrahydrofuran (2.77 ml). The solution is cooled to −20° C. and a 10% solution of isoamyl nitrite in dry dimethylformamide (1.12 ml, 0.83 mmol) is added with stirring. The solution is stirred for 30 minutes at −20° C. and then cooled to −25° C. Triethylamine (0.7 ml) is slowly added until the solution is slightly alkaline, pH 8–9. While stirring at −20° C., a solution of N-[N-[N-(N-L-leucyl)-L-arginyl]-L-prolyl]glycinamide diacetate (V, Example 15, 0.427 g, 0.762 mmol) in dry dimethylformamide (4.5 ml) and triethylamine (0.28 ml) is added. The resulting solution is stirred at −20° C. for 30 minutes, at 0° C. for 30 minutes and at ice bath temperature for 18 hours. The solution is filtered and the precipitate is washed with dry dimethylformamide (2×2 ml). The combined filtrates are concentrated under reduced pressure at 40° C. The residue is dissolved in methanol (5 ml), and diethyl ether (500 ml) is slowly added. The precipitate is collected, dried and purified by partition chromatography on a chemically modified cross-linked dextran ("Sephadex LH-20") using the lower phase of n-butanol-acetic acid-water (8:4:40). The combined fractions are concentrated to dryness under reduced pressure at 45° C., dissolved in methanol (5 ml), and added to diethyl ether (250 ml). The precipitate is collected by filtration and dried to yield the title compound with $[\alpha]_D^{25}$ −53.50° (c = 1.0, 1% aqueous acetic acid), isolated as the diacetate salt.

Amino acid analysis gives the following composition:

| Histidine | 1.0 | 1.04 | Proline | 0.96 | 1.03 |
| --- | --- | --- | --- | --- | --- |
| Arginine | 0.95 | 0.93 | Glycine | 2.01 | 1.98 |
| Serine | 0.90 | 0.86 | Leucine | 0.86 | 1.02 |
| Glutamic Acid | 1.07 | 1.04 | Tyrosine | 1.12 | 1.04 |

Electrophoresis at pH 1.6 in 8% aqueous formic acid and at 3500 volt gives a single spot and shows the uniformity of the compound.

In the same manner, when using t-butyl nitrite instead of isoamyl nitrite, the title compound is also obtained.

If desired, the above diacetate salt is treated with Amberlite IRA-400 or IRA-410, previously converted to a salt thereof with a pharmaceutically acceptable acid. Elution yields the corresponding salt of the title compound. Alternatively, the above diacetate salt is treated in aqueous solution with an alkali metal salt of tannic, alginic, or pamoic acid and the corresponding tannate, alginate or pamoate salt of the hormone is isolated by filtration or centrifugation.

We claim:
1. N-[N-(N-Carboxy-N$^G$-nitro-L-arginyl)-L-prolyl]-glycinamide N-t-butyl ester.

* * * * *